(12) United States Patent
Goodson

(10) Patent No.: US 7,655,036 B2
(45) Date of Patent: Feb. 2, 2010

(54) BIFURCATED ENDOLUMINAL PROSTHETIC ASSEMBLY AND METHOD

(75) Inventor: Burt Goodson, Fremont, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 851 days.

(21) Appl. No.: 10/131,902

(22) Filed: Apr. 24, 2002

(65) Prior Publication Data

US 2004/0111148 A1 Jun. 10, 2004

(51) Int. Cl.
*A61F 2/06* (2006.01)

(52) U.S. Cl. ........................ 623/1.35; 623/1.16

(58) Field of Classification Search ............... 623/1.35, 623/1.13, 1.16
See application file for complete search history.

(56) References Cited

U.S. PATENT DOCUMENTS

| 5,607,464 | A | | 3/1997 | Trescony et al. |
| 5,683,449 | A | | 11/1997 | Marcade |
| 5,755,773 | A | | 5/1998 | Evans et al. |
| 6,033,434 | A | * | 3/2000 | Borghi ..................... 623/1.35 |
| 6,051,020 | A | * | 4/2000 | Goicoechea et al. ....... 623/1.35 |
| 6,093,203 | A | | 7/2000 | Uflacker |
| 6,102,938 | A | | 8/2000 | Evans et al. |
| 6,143,022 | A | | 11/2000 | Shull et al. |
| 6,149,682 | A | * | 11/2000 | Frid ........................ 623/1.35 |
| 6,162,246 | A | * | 12/2000 | Barone ..................... 623/1.35 |
| 6,238,432 | B1 | | 5/2001 | Parodi |
| 6,344,052 | B1 | | 2/2002 | Greenan et al. |

FOREIGN PATENT DOCUMENTS

| WO | WO 9745073 A | 12/1997 |
| WO | WO 0018322 A | 4/2000 |
| WO | WO 0174273 A | 10/2001 |

* cited by examiner

*Primary Examiner*—Corrine M McDermott
*Assistant Examiner*—Christopher D Prone
(74) *Attorney, Agent, or Firm*—Anthony Sheldon (57) ABSTRACT

The invention provides a bifurcated endoluminal prosthetic assembly. The assembly includes a trunk body including a body lumen and at least one access port. At least one branch body is positioned adjacent the access port. The branch body includes a branch lumen in communication with the body lumen. The assembly further includes a ring including at least one connector operably attached to the branch body. The ring is sized to operably engage the trunk body. The ring retains the branch body adjacent the access port. The invention further provides a method of retaining a branch body adjacent a bifurcated endoluminal prosthetic assembly. A ring operably attached to the branch body is compressed. The ring is positioned within the endoluminal prosthetic assembly. The compressed ring is expanded into operable engagement with the endoluminal prosthetic assembly.

15 Claims, 5 Drawing Sheets

FIG. 2B – Top View

FIG. 2A – Side View

FIG. 3B – Top View

FIG. 3A – Side View

BIFURCATED ENDOLUMINAL PROSTHETIC ASSEMBLY AND METHOD

TECHNICAL FIELD OF THE INVENTION

The present invention relates generally to the field of implantable medical devices. More particularly, the invention relates to a bifurcated endoluminal prosthetic assembly and method including improved branch body retention.

BACKGROUND OF THE INVENTION

Abdominal aortic aneurysms (AAA) represent one of the most common types of aneurysms and result in about 15,000 deaths annually in the United States. An aneurysm is produced when a thinning or weak spot in a vessel wall dilates eventually posing a health risk from its potential to rupture, clot, or dissect. An aneurysm frequently occurs in arteries, but may also form in veins. The etiology of aneurysm formation is not entirely understood, but is thought to be related to congenital thinning of the artery, atherosclerotic vessel degeneration, vessel trauma, infection, smoking, high blood pressure, and other causes leading to vessel degeneration. Left untreated, AAA may lead to gradual vessel expansion, thrombus formation leading to stroke or other vessel blockage, vessel rupture, shock, and eventual death.

AAA are generally localized on long abdominal aortic sections below the renal arteries and oftentimes extend into one or both of the iliac arteries. The aneurysm may begin with a small vessel distension that progressively enlarges at a variable and unpredictable rate. An AAA may enlarge at an average rate of about 0.3-0.5 cm per year. The AAA may continue to enlarge in a silent fashion until a catastrophic event, such as a rupture, occurs. The best predictor of rupture risk is size, wherein rupture is relatively uncommon in AAA less than 5 cm. Once reaching about 8 cm, however, there is about a 75 percent chance of rupture within a year. Besides rupture, another risk of AAA is thrombus dissection. As the vessel enlarges, a thrombus may develop in the aneurysm due to perturbations in blood flow dynamics. Pieces of the clot may eventually loosen and carry away, eventually forming blockages in the legs, lungs, or brain.

AAA are most commonly treated in open surgical procedures, where the diseased vessel segment is bypassed and repaired with an artificial vascular graft. While considered to be an effective surgical technique, particularly considering the alternative of the usually fatal ruptured AAA, conventional vascular graft surgery suffers from a number of disadvantages. The surgical procedure is complex and requires experienced surgeons and well equipped surgical facilities. Even with the best surgeons and equipment, patients suffering from such aneurysms are often elderly and weakened from cardiovascular and other diseases. This factor reduces the number of patients eligible for surgery. Even for eligible patients prior to rupture, conventional aneurysm repair has a relatively high mortality rate, usually from 2 to 10%. Morbidity related to the conventional surgery includes myocardial infarction, renal failure, impotence, paralysis, and other conditions. Even with successful surgery, recovery takes several weeks and often requires a lengthy hospital stay.

To overcome some of the drawbacks associated with open surgery, a variety of endovascular prosthesis placement techniques have been proposed. Without the need for open abdominal surgery, patient complications and recovery time may be significantly reduced. One endovascular AAA repair technique involves a tubular prosthesis deployed by remote insertion through a femoral artery. The prosthesis may include a synthetic graft sheath body supported by an expandable structure such as a stent. The stent may be self-expanding or balloon-expanding and typically is the means for anchoring the prosthesis to the vessel wall. The stent-graft prosthesis acts as a shunt to carry blood flow from a healthy portion of the aorta, through the aneurysm, and into one or both of the iliac artery branches. The prosthesis excludes any thrombus present in the aneurysm while providing mechanical reinforcement of the weakened vessel reducing the risk of dissection and rupture, respectively.

A number of endovascular AAA stent-graft prosthesis designs are known. For aneurysms proximal to the iliac arteries, many of the designs utilize bifurcated structures. Bifurcated stent-graft prostheses generally have a trunk portion with a relatively large lumen deployed in the aorta, and first and second branch portions with smaller branch lumens deployed within each of the iliac arteries. The deployed trunk and branch portions preferably seal to each other and to the healthy vascular walls beyond the aneurysm to isolate the aneurysm from the bloodstream. Advantageously, the aortic blood flow enters the trunk prosthetic lumen, is separated into the two branch prosthetic lumens, and then flows into each of the iliac arteries in a path that approximates that of a normal, healthy vascular system.

A variety of minimally invasive techniques have been suggested for deployment of these bifurcated prostheses, including in situ assembly of multiple prosthetic modules. The primary stent-graft module may include a trunk, a first branch, and a shortened branch. A secondary stent-graft module may include a second branch for operable attachment to the shortened branch of the primary module. In a number of stent graft designs, the second stent-graft module is operably attached by slipping onto or into the shortened branch thereby providing a length of surface overlap. Frictional forces between the overlapping surfaces usually prevent the second branch from detaching from the primary stent-graft module.

Endovascular deployment and assembly of the multiple prosthetic modules may begin whereby the primary stent-graft module is deployed by catheter through a vessel, such as the femoral artery. The trunk may be positioned and attached to the aorta while the first branch may extend into a single iliac artery. The shortened branch may be oriented toward the contralateral, or alternate, iliac artery. The second branch may then be deployed by catheter through the contralateral iliac to the shortened branch of the primary module. The second branch may be operably attached to the shortened branch thereby completing assembly of the continuous bifurcated prosthetic lumen. Such deployment of the second branch can be very straightforward, and in situ assembly of bifurcated prostheses appears to hold significant promise for many abdominal aortic aneurysm patients.

One shortcoming associated with the multi-module prosthetic stent-graft relates to module separation. The AAA may vary widely in location, size, and the distended shape of the aneurysm itself. Particularly after treatment, the aneurysm and associated vessels may drastically change morphology thereby exerting stress forces on the deployed stent-graft. A significant amount of stress may be exerted on the joint between the shortened branch and second branch. With sufficient change in aneurysm morphology and subsequent stress placed on the joint, the module pieces may separate. The patient may have to undergo another treatment given the problem is detected early. Undetected module separation may lead to continued leakage, aneurysm regrowth, and even the more serious problems associated with AAA. Accordingly, it would be advantageous to prevent separation of the stent-graft modules.

Therefore, it would be desirable to provide a bifurcated endoluminal prosthesis including improved contralateral branch docking that overcomes the aforementioned and other disadvantages.

SUMMARY OF THE INVENTION

An aspect according to the present invention provides a bifurcated endoluminal prosthetic assembly. The assembly includes a trunk body including a body lumen and at least one access port. At least one branch body is positioned adjacent the access port. The branch body includes a branch lumen in communication with the body lumen. The assembly further includes a ring including at least one connector operably attached to the branch body. The ring is sized to operably engage the trunk body. The ring retains the branch body adjacent the access port. The connector may provide a relative range of motion between the branch body and the ring. The connector may maintain a fixed relative position of the branch body and the ring. At least one latch portion adapted to interlock with a portion of the trunk body may be operably attached to the ring. The ring may include at least one radiopaque marker and/or a biocompatible membrane disposed on a support element. The ring may include a ring diameter greater than an access port diameter. The ring may expand from a collapsed ring form to an expanded ring form. The expandable ring may be an expandable stent and/or may self-expand or balloon-expand. The expandable ring may include an expanded ring diameter greater than a body lumen diameter. The access port may be adapted to receive the collapsed ring form.

Another aspect according to the invention provides a method of retaining a branch body adjacent a bifurcated endoluminal prosthetic assembly. A ring operably attached to the branch body is compressed. The ring is positioned within the endoluminal prosthetic assembly. The compressed ring is expanded into operable engagement with the endoluminal prosthetic assembly. A relative range of motion may be provided between the branch body and the ring. A fixed relative position of the branch body and the ring may be maintained. Expanding the compressed ring may include self-expanding the ring or balloon-expanding the ring. The operable engagement may include frictional surface contact and/or interlocking surface contact.

Another aspect according to the invention provides a bifurcated endoluminal prosthetic assembly including a branch body retained adjacent the assembly. The assembly includes a ring including means for operably attaching the ring to the branch body, and means for positioning the compressed ring within the endoluminal prosthetic assembly. The assembly further includes means for expanding the compressed ring into operable engagement with the endoluminal prosthetic assembly. Means may be included for providing a relative range of motion between the branch body and the ring, and for maintaining fixed relative position of the branch body and the ring.

DETAILED DESCRIPTION

Figure 1A:
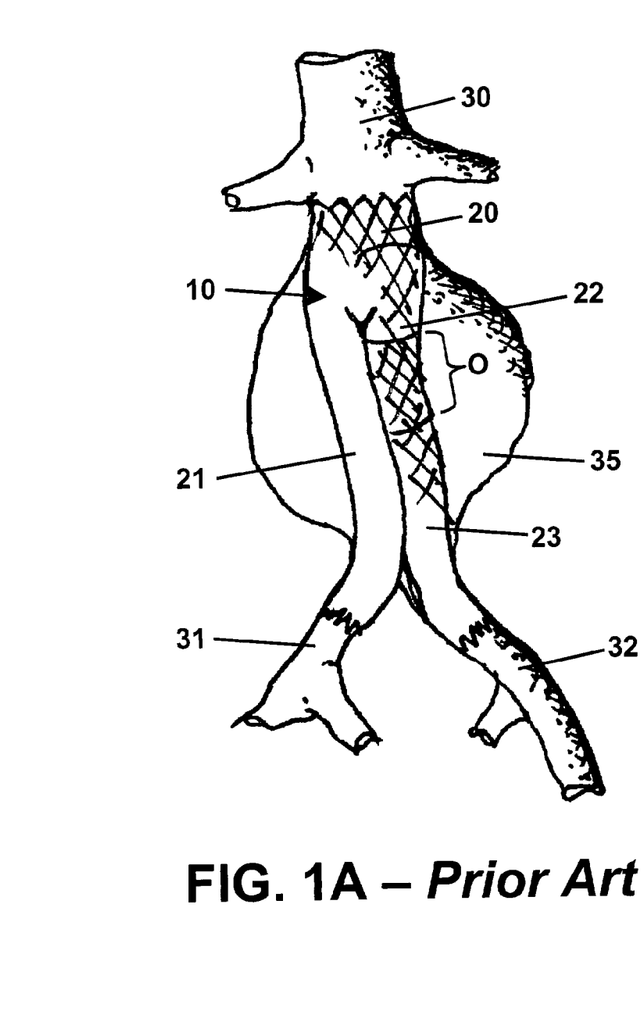
FIGS. 1A and 1B are sequential views of a prior art endoluminal prosthetic assembly deployed in an abdominal aortic aneurysm.
Figure 1B:
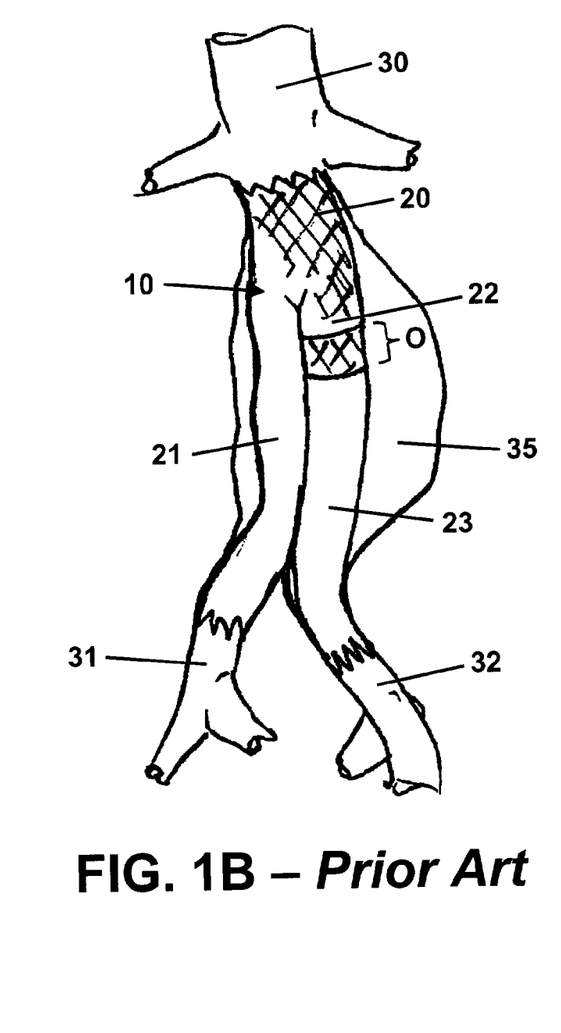

Referring to the drawings, wherein like reference numerals refer to like elements, FIGS. 1A and 1B are sequential views of a prior art endoluminal prosthetic assembly 10 deployed in an abdominal aortic aneurysm 35 as it heals. Assembly 10 includes a tubular trunk body 20, a first branch body 21, and a shortened branch body 22. A second branch body 23 is operably attached to the shortened branch body 22. Trunk body 20 includes a relatively large lumen and is deployed in patient aorta 30. Trunk body 20 lumen bifurcates into smaller branch lumens of the first branch body 21 and second branch body 23. The branch bodies 21, 23 are deployed within first iliac artery 31 and second iliac artery 32. The deployed trunk body 20 and branch bodies 21, 23 preferably seal to each other and to the healthy vascular walls beyond the aneurysm 35 isolating the aneurysm 35 from the bloodstream. As previously described, aortic blood flow enters the trunk body 20 lumen, is separated into the two branch portions 21, 23, and then flows into each of the iliac arteries 31, 32 in a path that approximates that of a normal, healthy vascular system.

FIG. 1A shows position of assembly 10 in abdominal aortic aneurysm 35 soon after deployment. Second branch body 23 is operably attached by slipping onto or into the shortened branch body 22 thereby providing a length of surface overlap, O. Frictional forces between the overlapping surfaces usually prevent the second branch body 23 from detaching from the trunk body 20.

As the aneurysm 35 heals, the site may undergo morphological changes as shown in FIG. 1B. These changes may produce stress forces on the assembly 10. For example, trunk body 20 may be pulled in an opposite direction from the second branch body 23. As a result, the length of surface overlap, O, may shorten. Continued changes in aneurysm 35 morphology may result in reduced surface overlap, O, and eventual separation of second branch body 23 from trunk body 20.

Figure 2A:
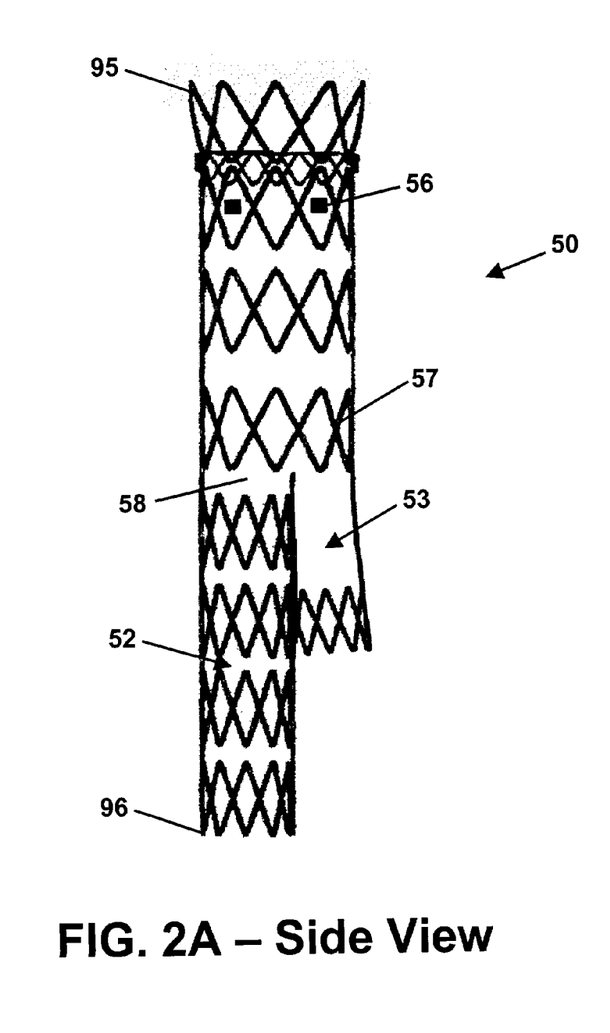
FIGS. 2A and 2B are side and top views of a trunk body used for aneurysm repair.
Figure 2B:
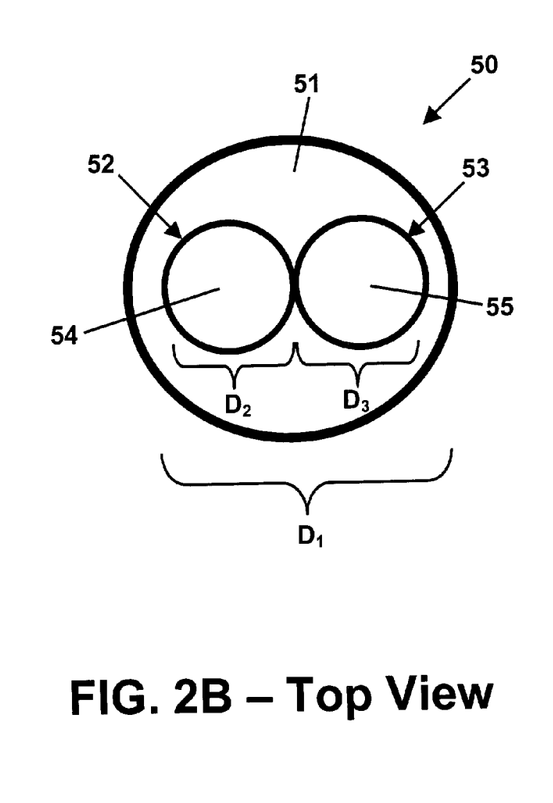

Referring now to side and top views FIGS. 2A and 2B, a trunk body 50 includes a body lumen 51 and at least one access port. In one embodiment, trunk body 50 may be tubular in shape and include a first branch body 52 and a shortened branch body 53, which forms the access port. In the following description, access port and shortened branch body 53 refer to the same element. The shortened branch body 53 size, number, and geometry may vary, but is generally adapted to receive and seal to an additional branch body. Body lumen 51 bifurcates into a first branch lumen 54 and shortened branch lumen 55, for diverting blood flow. At least one marker 56 may be disposed on the trunk body 50, first branch body 52, and/or shortened branch body 53 facilitating positioning of trunk body 50 in situ. In one embodiment, marker 56 may be a radiopaque marker visualized by fluoroscopy. Those skilled in the art will recognize that the size, nature, number, and geometry of the marker 56, as well as the method of visualization, may vary to provide effective device positioning.

Trunk body 50 may be formed from a variety of materials used for expandable prosthetic devices known in the art. For example, trunk body 50 may include covered stent design elements disclosed in U.S. Pat. No. 6,143,022 issued to Shull et al. Trunk body 50 may further include pleated structure design elements disclosed in U.S. Pat. No. 5,607,464 issued to Trescony et al. First branch body 52 and shortened branch body 53 may be formed from like materials as trunk body 50. Those skilled in the art will recognize that trunk body 50 geometry, size, and construction may vary without diminishing the utility of the present invention.

Trunk body 50 may be formed from a plurality of support elements 57, such as a mesh of wires welded together at points of contact. Support elements 57 may be manufactured from a resilient material known in the art, such as Nitinol, titanium, tantalum, stainless steel, metal alloy, polymer, and other biocompatible material capable of maintaining an expanded shape inside the vessel in which the device is deployed. Graft material 58 may be disposed outside or inside of the support elements 57. Graft material 58 may include any number of biocompatible, blood-impermeable graft membranes known in the art, such as polyester, polyethylene, polytetrafluoroethylene (PFTE), polyurethane, propylene, nylon, and the like. Graft material 58 may be secured to support elements 57 with a variety of strategies known in the art. Examples include suturing, adhesive bonding, heat welding, ultrasonic welding, and the like. Trunk body 50 and first branch body 52 may include flared portions 95, 96 for vessel wall attachment. Flared portions 95, 96 may include stent elements, with or without graft material, that project radially from trunk body 50 and first branch body 52 thereby increasing frictional contact with the vessel wall.

Trunk body 50, first branch body 52, and shortened branch body 53 may expand from a collapsed form into an expanded form facilitating intravascular deployment. In one embodiment, trunk body 50 may deploy to a diameter, $D_1$, of about 15 to 30 mm. First branch body 52 and shortened branch body 53 may deploy to diameters, $D_2$ and $D_3$, of about 5 to 15 mm. In another embodiment, deployed diameter, $D_1$, may be chosen in dependency of the internal diameter of the intact infrarenal aorta portion positioned upstream of an abdominal aortic aneurysm. Likewise, deployed diameters, $D_2$ and $D_3$, may be chosen in dependency of the internal diameter of the intact iliac portion positioned downstream of the aneurysm. In yet another embodiment, trunk body 50 deployed diameter, $D_1$, and first branch body 52 and shortened branch body 53 deployed diameters, $D_2$ and $D_3$, may be varied as required for deployment in a vessel other than an abdominal aorta. Furthermore, first branch body 52 and shortened branch body 53 need not have equivalent deployed diameters.

Figure 3A:
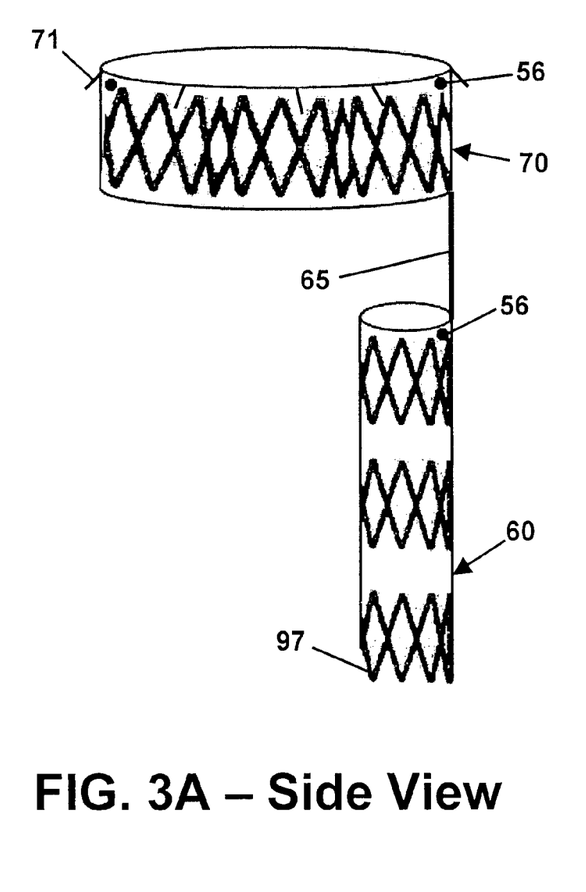
FIGS. 3A and 3B are side and top views of a second branch body and ring configuration in accordance with the present invention.
Figure 3B:
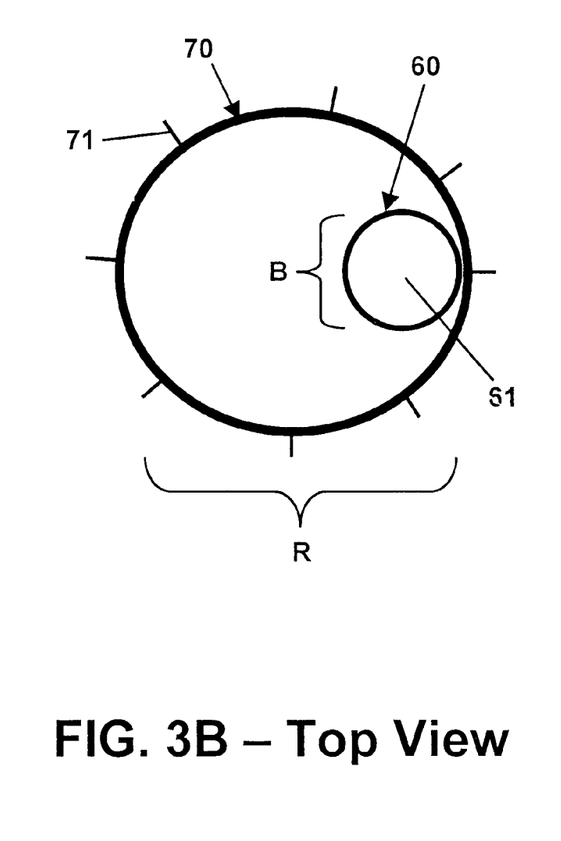

Referring now to side and top views FIGS. 3A and 3B, a second branch body 60 includes a second branch lumen 61 formed therein. At least one marker 56 may be disposed on the second branch body 60 and/or ring 70 facilitating positioning in situ. Ring 70 may include at least one latch portion 71 adapted to interlock with a portion of the trunk body. In one embodiment, latch portion 71 may be a plurality of barbs positioned around the circumference of the ring 70. Barbs may be manufactured from a rigid material, such as biocompatible plastic or metal, and adapted to insert into the trunk body support elements and/or graft material. In another embodiment, latch portion 71 may be any number of structures designed to interlock with a portion of the trunk body. Latch portion 71 (e.g., barbs) may be adapted not compromise the leak free nature of the material thereby minimizing any leaks into the aneurysm. Those skilled in the art will recognize that the geometry, size, and number of the latch portion 71 may vary while still providing interlocking surface contact between the ring 70 and trunk body.

Second branch body 60 and ring 70 may be formed from a variety of materials used for expandable prosthetic devices known in the art. In one embodiment, second branch body 60 and ring 70 may be formed from like materials and structural elements as trunk body. In another embodiment, second branch body 60 and ring 70 may be an expandable stent, either self-expanding or balloon-expandable as known in the art. Second branch body 60 and ring 70 may include a biocompatible membrane, such as a graft material, disposed on a support element as described for the trunk body 50. Second branch body 60 may include flared portion 97 for vessel wall attachment, as previously described.

Ring 70 may expand from a collapsed form into an expanded form facilitating intravascular deployment. Ring 70 is sized to operably engage the trunk body. In one embodiment, ring 70 may deploy to a diameter, R, chosen in dependency of the trunk body deployed diameter, $D_1$. For example, ring 70 deployed diameter, R, may be about 15 to 30 mm, slightly larger than the trunk body deployed diameter, $D_1$. A slightly larger diameter size of the ring 70 may provide operable engagement between ring 70 and trunk body surfaces. In another embodiment, ring 70 deployed diameter, R, may be chosen in dependency of the deployed diameter of the shortened branch body, $D_3$. For example, ring 70 deployed diameter, R, may be larger than the shortened branch body deployed diameter, $D_3$. As such, expanded ring 70 is too large to slip through shortened branch body 60 once deployed.

Second branch body 60 may expand from a collapsed form into an expanded form facilitating intravascular deployment. In one embodiment, second branch body 60 may be sized to operably engage the shortened branch body and/or the intact iliac portion positioned downstream of the aneurysm. For example, one portion of the second branch body 60 may deploy to a diameter, B, of about 5 to 15 mm, slightly larger than the shortened branch body deployed diameter, $D_3$. Another portion of the second branch body 60 may deploy to a diameter slightly larger than the internal diameter of the iliac artery. Various portions of the second branch body 60 may be deployed into a sealed surface contact (e.g., by using a slightly larger deployed diameter) with the shortened branch body and iliac artery. As such, the second branch body 60 may minimize fluid leaks into the aneurysm.

Ring 70 includes at least one connector 65 operably attached to the second branch body 60. In one embodiment, connector 65 may include at least one flexible member adapted to provide a relative range of motion between the second branch body 60 and ring 70. The flexible member may be formed from an elastomeric material, such as a biocompatible polymer, to provide a degree of free motion. In another embodiment, connector 65 may include at least one rigid member adapted to provide a fixed relative position of the second branch body 60 and ring 70. The rigid member may be formed from a rigid material, such as a biocompatible plastic or metal, to provide a fixed connection angle. In another embodiment, connector 65 may include at least one rigid member adapted to provide a relative range of motion through one or more hinged joints (not shown) operably attached to said member.

FIGS. 4A, 4B, 4C, and 4D are sequential views of an endoluminal prosthetic assembly being deployed in an abdominal aortic aneurysm. Those skilled in the art will recognize that deployment of the endoluminal prosthetic assembly is not limited to the described strategy. Numerous modifications, substitutions, and variations may be made to the strategy while providing effective endoluminal prosthetic assembly deployment consistent with the present invention.

Figure 4A:
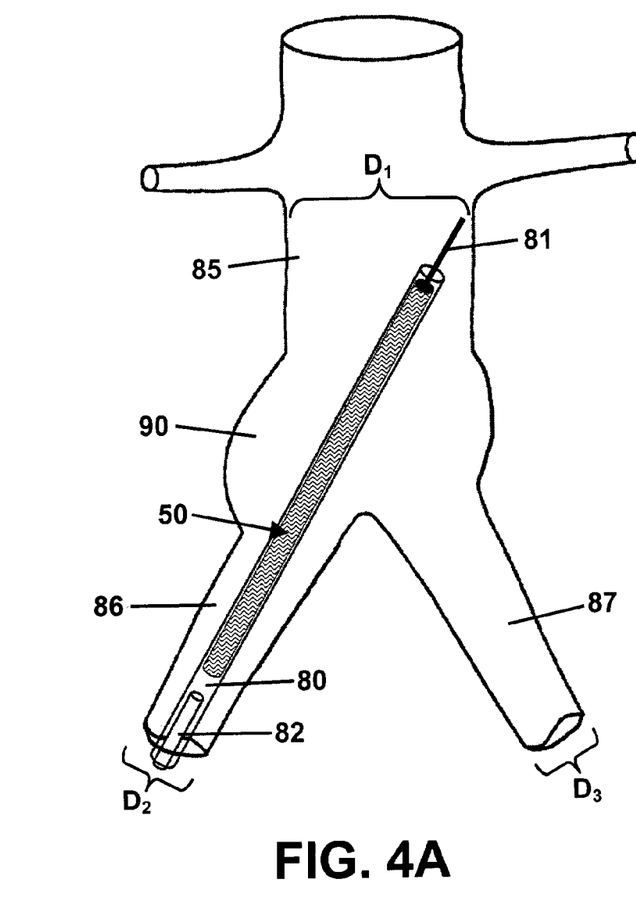
FIGS. 4A, 4B, and 4C, and 4D are sequential views of an endoluminal prosthetic assembly being deployed in an abdominal aortic aneurysm, in accordance with the present invention.

As shown in FIG. 4A, trunk body 50 may be compressed within a flexible catheter 80 or other adequate delivery device as known in the art. In another embodiment, trunk body 50 may be compressed and disposed on a catheter-expandable balloon (not shown) for deployment. A guide wire 81 may be positioned into the abdominal aorta 85 via patient femoral artery. Catheter 80 may then be advanced through first iliac artery 86 and into abdominal aorta 85 along pre-positioned guide wire 81. Trunk body 50 may then be positioned substantially within abdominal aorta 85 and first iliac artery 86 branch. Trunk body 50 position may be determined by visualization methods known in the art, such as fluoroscopy and/or intravascular ultrasound (IVUS). In one embodiment, radiopaque markers disposed on portion of the trunk body 50 and/or catheter 80 may be visualized by fluoroscopy.

After appropriate catheter 80 positioning, trunk body 50 may be deployed. A push rod 82 or other axially fixing structure may be maintained in a fixed contact position with trunk body 50 as catheter 80 is withdrawn axially. Trunk body 50 may self-expand as catheter 80 is withdrawn or be balloon expanded to a deployed diameter, $D_1$. Trunk body 50 deployed diameter, $D_1$, may vary as required by application. A portion of the trunk body 50 may be expanded into contact with abdominal aorta 85. As catheter 80 is further withdrawn, first branch body and shortened branch body may expand into first iliac artery 86 and second iliac artery 87, respectively, to deployed diameters, $D_2$ and $D_3$. The deployed diameters, $D_2$ and $D_3$, may vary as required by application. In one embodiment, first and shortened branch bodies may be expanded into contact with respective iliac arteries 86, 87. The trunk body 50 to aorta 85 contact and the branch body to iliac artery 86, 87 contact is intended to provide a fluid seal minimizing blood flow into aneurysm 90.

Figure 4B:
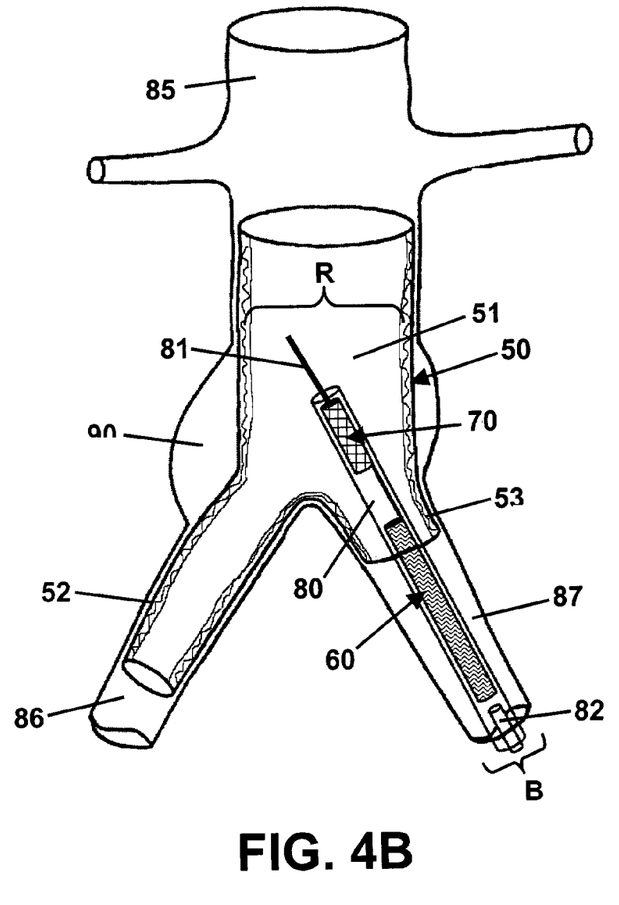
Figure 4C:
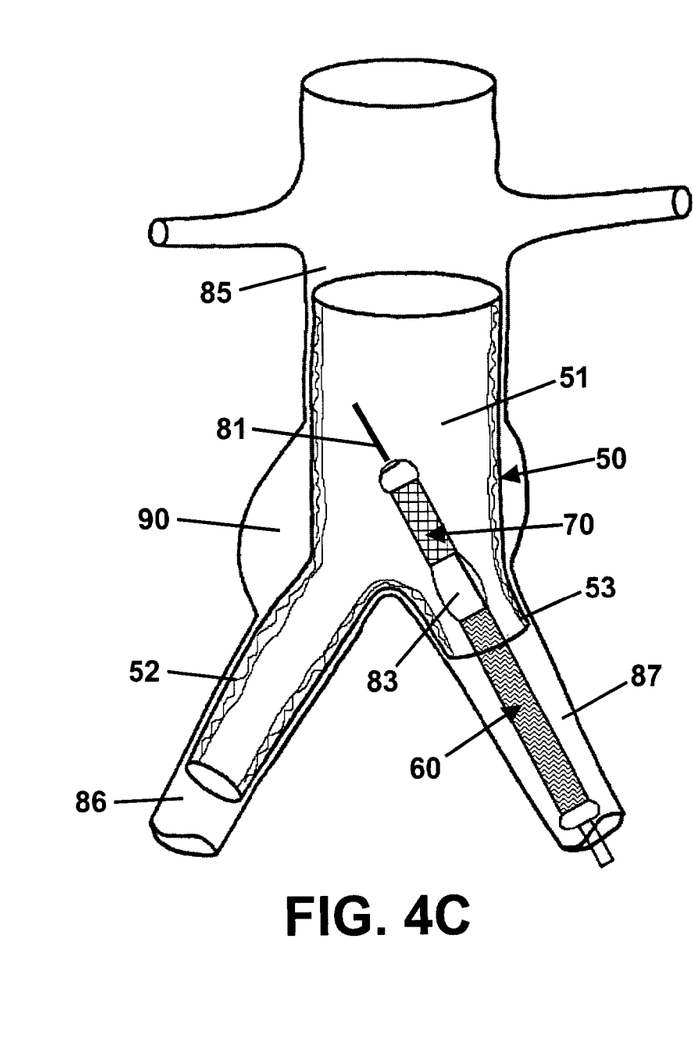

Catheter 80 and guide wire 81 may be removed from patient, leaving trunk body 50, first branch body 52, and shortened branch body 53 in the deployed state shown in FIG. 4B. Ring 70 and second branch body 60 may be compressed within a flexible catheter 80 or other prosthesis delivery device as known in the art. In another embodiment shown in FIG. 4C, ring 70 and/or second branch body 60 may be may be compressed and disposed on a catheter-expandable balloon 83 for deployment. Referring again to FIG. 4B, guide wire 81 may be inserted via a contralateral femoral artery, and advanced through second iliac artery 87, through shortened branch body 53, and into trunk body lumen 51. Catheter 80 may then be advanced through second iliac artery 87 and into abdominal aorta 85 along pre-positioned guide wire 81. The shortened branch body 53 may be adapted to receive the collapsed ring 70 form. For example, the shortened branch body 53 deployed diameter, $D_3$, size may allow passage of a smaller collapsed ring 70 size. Ring 70 may be positioned within trunk body lumen 51. Second branch body 60 may be positioned partially within the trunk body lumen 51, extending into the second iliac artery 87. Ring 70 and second branch body 60 position may be determined by visualization methods as known in the art. In one embodiment, radiopaque markers disposed on ring 70, second branch body 60, and/or catheter 80 may be visualized by fluoroscopy.

After appropriate catheter 80 positioning, ring 70 and second branch body 60 may be deployed. A push rod 82 or other axial positioning structure may be maintained in a fixed contact position with second branch body 60 as catheter 80 is withdrawn axially. In one embodiment, ring 70 may self-expand to a deployed diameter, R, as catheter 80 is withdrawn. In another embodiment shown in FIG. 4C, ring 70 and second branch body 60 may be expanded by the catheter-expandable balloon 83. Referring again to FIG. 4B, ring 70 deployed diameter, R, may vary as required by application. Ring 70 may be expanded into operable engagement with trunk body 50. The operable engagement may include frictional forces between contacting ring 70 and trunk body 50 surfaces. In addition, the operable engagement may include interlocking ring 70 and trunk body 50 surface contact. In one embodiment, the latch portion provides means for interlocking surface contact. In another embodiment, any number of complementary surface features may be used to provide sliding or interlocking surface contact and/or enhance frictional forces between surfaces.

As catheter 80 is further withdrawn, second branch body 60 may expand to deployed diameter, B. Second branch body 60 deployed diameter, B, may vary as required by application. In one embodiment, second branch body 60 may be expanded into contact with the shortened branch body 53. Another portion of the second branch body 60 may expand into contact with the second iliac artery 87. The second branch body 60 to shortened branch body 53 contact and the second branch body 60 to second iliac artery 87 contact may provide a fluid seal minimizing blood flow into aneurysm 90.

Figure 4D:
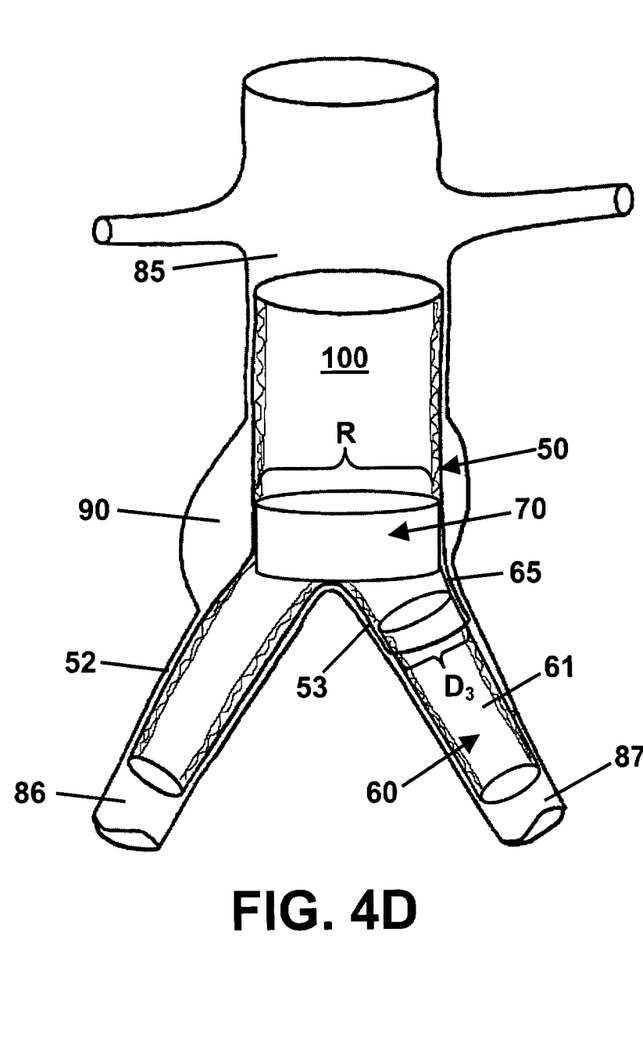

Catheter 80 and guide wire 81 are then removed from patient, leaving the bifurcated endoluminal prosthetic assembly 100 in the fully deployed and assembled state shown in FIG. 4D. Assembly 100 includes the trunk body 50, second branch body 60 positioned adjacent the shortened branch body 53, and ring 70 including connector 65 operably attached to the second branch body 60. Second branch lumen 61 is in fluid communication with the body lumen 51. The shortened branch body 53 may seal to the second branch body 60.

Several features may provide retention of second branch body 60 adjacent the shortened branch body 53. The expansion of the second branch body 60 into frictional surface contact with the shortened branch body 53 may provide a first retention feature. The operable engagement between ring 70 and trunk body 50 may provide a second retention feature. The operable engagement may include interlocking surface contact (e.g., provided by latch portion such as barbs) and/or frictional surface contact. Specifically, contact of the second branch body 60 and trunk body 50 surfaces may provide the frictional surface contact. The ring 70 may be sized to prevent slippage through the shortened branch body 53 thereby providing a third retention feature. Specifically, the expanded ring 70 deployed diameter, R, is larger than the shortened branch body 53 diameter, $D_3$. Therefore, if the operable engagement between the expanded ring 70 and trunk body 50 fails, the expanded ring 70 will not slip through a smaller sized shortened branch body 53. The retention features used singularly or in combination may prevent separation of second branch body 60 from the shortened branch body 53.

Connector 65 may provide a relative range of motion between the ring 70 and second branch body 60 thereby providing an additional retention feature. A flexible or hinged connection may allow ring 70 to move with respect to second branch body 60 thereby adapting to changes in aneurysm morphology. Providing the relative range of motion may reduce stress forces placed on the components thereby reducing risk of component separation. In another embodiment, connector 65 may provide a fixed relative position of the second branch body 60 and ring 70. A rigid connection may maintain a fixed angle between the ring 70 and second branch body 60 for when a flexible connector is not required.

Various changes and modifications may be made to the embodiments disclosed herein without departing from the spirit and scope of the invention. For example, the bifurcated endoluminal prosthetic assembly configuration, and method of deploying the same are not limited to any particular design or sequence. Specifically, the trunk body, branch bodies, ring, and connector geometry, size, arrangement, number, material, features, method of expansion, and deployment step order may vary without limiting the utility of the invention. Upon reading the specification and reviewing the drawings hereof, it will become immediately obvious to those, skilled in the art that myriad other embodiments according to the present invention are possible.

The invention claimed is:

1. A bifurcated endoluminal prosthetic assembly, comprising:
    a trunk body including a body lumen;
    a first branch body having a first branch body lumen in communication with the trunk body lumen;
    a shortened branch body having a shortened branch body lumen in communication with the trunk body lumen and at least one access port wherein the lumen has a shortened branch body lumen diameter;
    a second branch body positioned adjacent the access port, the second branch body including a second branch body lumen in communication with the trunk body lumen;
    a ring positioned within the trunk body lumen and spaced apart from the second branch body, the ring sized to operably engage the trunk body at a region of the trunk body distal to the first branch body and second branch body and wherein the ring diameter is greater than the shortened branch body lumen diameter; wherein the ring retains the second branch body adjacent the access port, and
    an elongated connector spanning between the ring and the second branch body, the connector connected at one end to the ring and at another end to the second branch body.

2. The assembly of claim 1 wherein the connector provides a relative range of motion between the second branch body and the ring.

3. The assembly of claim 1 wherein the connector maintains a fixed relative position of the second branch body and the ring.

4. The assembly of claim 1 further comprising at least one latch portion operably attached to the ring, wherein the latch portion is adapted to interlock with a portion of the trunk body.

5. The assembly of claim 1 wherein the ring comprises at least one radiopaque marker.

6. The assembly of claim 1 wherein the ring comprises a biocompatible membrane disposed on a support element.

7. The assembly of claim 1 wherein the ring comprises an expandable ring, wherein the expandable ring expands from a collapsed ring form to an expanded ring form.

8. The assembly of claim 7 wherein the expandable ring comprises an expandable stent.

9. The assembly of claim 7 wherein the expandable ring comprises a self-expanding ring.

10. The assembly of claim 7 wherein the expandable ring comprises a balloon-expandable ring.

11. The assembly of claim 7 wherein the expandable ring comprises an expanded ring diameter greater than a body lumen diameter.

12. The assembly of claim 7 wherein the access port is adapted to receive the collapsed ring form.

13. A bifurcated endoluminal prosthetic assembly, comprising:
    a trunk body including a body lumen having a trunk body diameter;
    a first branch body extending from the trunk body, the first branch body including a branch lumen in communication with the body lumen;
    a shortened branch body extending from the trunk body, the shortened branch body including an access port wherein the lumen has a shortened branch body diameter; and
    a ring including at least one connector, the ring spaced apart from and operably attached to a second branch body via the at least one connector, the second branch body having an upper portion sealingly deployed in said access port, the ring being deployed in and engaged with an inside surface of said body lumen at a region of the trunk body distal to and adjacent the access port and having a deployed diameter approximating said body lumen diameter, wherein said at least one connector between said ring and said second branch body provides a retaining force to help retain said second branch body within the access port when a separating force tending to pull said second branch body out of said access port is present.

14. The assembly of claim 13, wherein the connector provides a relative range of motion between said second branch body said ring.

15. The assembly of claim 13 further comprising:
    at least one latch portion operably attached to the ring, wherein the latch portion is adapted to interlock with a portion of the trunk body.

* * * * *